US005616217A

United States Patent [19]
Taylor

[11] Patent Number: 5,616,217
[45] Date of Patent: Apr. 1, 1997

[54] CONTROLLED ALKALI TREATMENT IN THE RECOVERY OF METHYL TERTIARY BUTYL ETHER

[75] Inventor: Mark E. Taylor, Orange, Tex.

[73] Assignee: Texaco Chemical Inc., White Plains, N.Y.

[21] Appl. No.: 516,030

[22] Filed: Aug. 17, 1995

[51] Int. Cl.$^6$ .............................. B01D 3/40; B01D 3/42; C07C 41/00

[52] U.S. Cl. .................... 203/97; 203/3; 203/7; 203/85; 203/37; 203/78; 203/98; 203/DIG. 23; 568/699

[58] Field of Search ............................. 568/699; 203/1, 203/3, 7, 18, 84, 85, 96, 97, 98, 36, 78, DIG. 6, DIG. 16, 37, DIG. 23; 585/803; 436/908

[56] References Cited

U.S. PATENT DOCUMENTS

| | | | |
|---|---|---|---|
| 3,653,835 | 4/1972 | Brandel | 73/445 X |
| 3,670,764 | 7/1972 | Hinton et al. | 203/36 X |
| 3,990,952 | 11/1976 | Katzen et al. | 203/37 X |
| 4,334,964 | 6/1982 | Prezelj et al. | 203/97 X |
| 5,037,511 | 8/1991 | Dornhagen et al. | 568/699 X |
| 5,243,091 | 9/1993 | Kruse et al. | 568/699 X |
| 5,302,253 | 4/1994 | Lessard et al. | 203/3 X |

*Primary Examiner*—Robert J. Warden
*Assistant Examiner*—E. Leigh Dawson
*Attorney, Agent, or Firm*—Henry H. Gibson; James L. Bailey; Harold J. Delhommer

[57] ABSTRACT

In the manufacture of MTBE from TBA and methanol, acidic by-products formed during the etherification reaction are removed by fractionating the etherification reaction product in a first MTBE distillation column to provide a first lower boiling distillation fraction comprising isobutylene, MTBE, methanol and acidic by-products and a first higher boiling distillation fraction comprising methanol, TBA and water, fractionating the first higher boiling distillation fraction in a recycle distillation column to provide a lower boiling TBA recycle fraction and a higher boiling water fraction, recycling the higher boiling water fraction to the MTBE distillation column at a charge point above the charge point for the etherification reaction product, and adding aqueous sodium hydroxide to the recycled higher boiling water fraction in an amount sufficient to neutralize the acidic by-products charged to the MTBE distillation column.

11 Claims, 1 Drawing Sheet

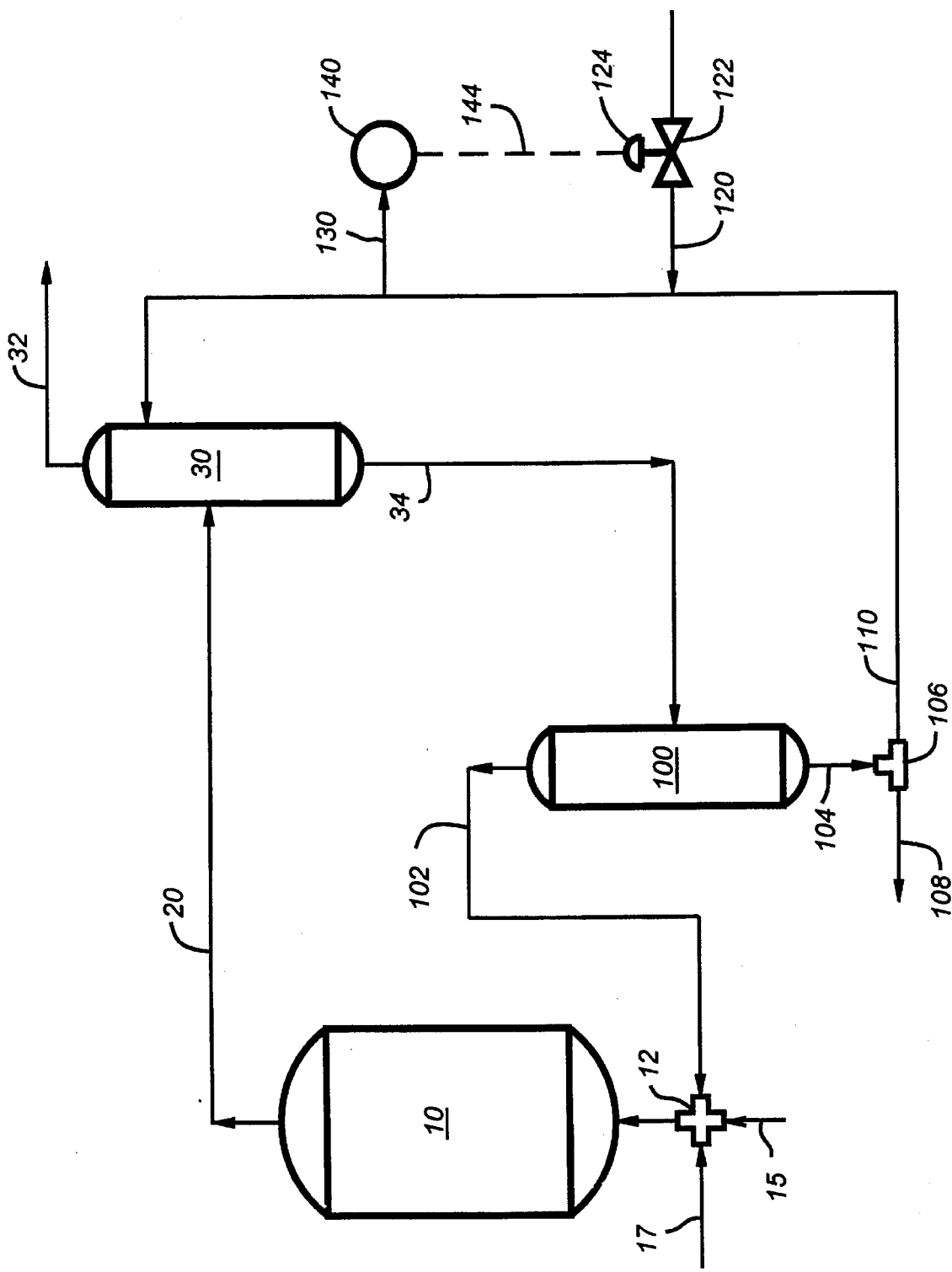

CONTROLLED ALKALI TREATMENT IN THE RECOVERY OF METHYL TERTIARY BUTYL ETHER

BACKGROUND OF THE INVENTION

1. Technical Field of the Invention

This invention relates to a method for the manufacture and purification of methyl tertiary butyl ether prepared from tertiary butyl alcohol and methanol. More particularly, this invention relates to a method for removing acidic by-products formed during the reaction of tertiary butyl alcohol with methanol.

Methyl tert-butyl ether is finding increasing use as a blending component in high octane gasoline as the current gasoline additives based on lead and manganese are phased out.

2. Prior Art

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate, the latter being azeotropically distilled to yield ether-methanol overhead which is recycled to water washing.

Kruse et al. U.S. Pat. No. 5,243,091, entitled "Method for the Manufacture and Recovery of Methyl Tertiary Butyl Ether", discloses a method for the preparation of methyl tertiary butyl ether wherein tertiary butyl alcohol is reacted with methanol to provide a reaction product comprising methyl tertiary butyl ether and by-product isobutylene and wherein the by-product isobutylene is reacted with methanol to provide additional methyl tertiary butyl ether and also a water washing method for the purification of the methyl tertiary butyl ether.

Gupta U.S. Pat. No. 5,292,964 discloses a process for the manufacture of methyl tertiary butyl ether from tertiary butyl alcohol and methanol wherein tertiary butyl alcohol is reacted with methanol in a primary reaction zone to provide a reaction product comprising methyl tertiary butyl ether, unreacted tertiary butyl alcohol, unreacted methanol and water, wherein the reaction product is separated in a distillation zone into a lighter fraction comprising substantially anhydrous methanol and methyl tertiary butyl alcohol and a heavier fraction comprising tertiary butyl alcohol, methanol and water, and wherein the lighter fraction is charged to a finishing reactor wherein the methanol is reacted with isobutylene to form additional methyl tertiary butyl ether.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl., Vses. Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process.

In Cassata et al. U.S. Pat. No. 5,395,982, filed Nov. 8, 1993, and entitled "Continuous Isobutylene-Assisted Aqueous Extraction of Methanol from Methyl Tertiary Butyl Ether," a process is disclosed wherein an impure methyl tertiary butyl ether product contaminated with isobutylene, methanol and water is purified by continuous countercurrent contact with water and isobutylene in a countercurrent contact extraction tower to provide an overhead raffinate comprising isobutylene, methyl tertiary butyl ether and water and an extract comprising methanol, water and a minor amount of methyl tertiary butyl ether, the overhead raffinate being separated in a methyl tertiary butyl ether purification distillation zone into a lighter distillation fraction comprising isobutylene and water and a heavier distillation fraction consisting essentially of methyl tertiary butyl ether, the lighter distillation fraction being decanted to remove water and to provide a distillate isobutylene fraction that is returned to the contact tower.

In copending Peters et al. U.S. patent application Ser. No. 08/299,391, filed Sep. 1, 1994, and entitled "Preparation of Methyl Tertiary Butyl Ether with Recycle" (D#81,148-D1), there is disclosed a process for the manufacture of methyl tertiary butyl ether from tertiary butyl alcohol and methanol and to the purification of a methanol-contaminated methyl tertiary butyl ether intermediate product formed during the process; the intermediate product being purified by countercurrent contact with water in an extraction tower, wherein isobutylene is added to the extraction tower to assist in the formation of an extract composed of methyl tertiary butyl ether, isobutylene and water and in the formation of a raffinate comprising methanol, isobutylene, residual methyl tertiary butyl alcohol and water.

SUMMARY OF THE INVENTION

This invention is directed to an improved method for the manufacture of methyl tertiary butyl ether from tertiary butyl alcohol and methanol and to the removal of acidic by-products formed during the reaction of tertiary butyl alcohol with methanol by charging the etherification reaction product to a first MTBE distillation column and fractionating it therein to provide a first lower boiling distillation fraction comprising isobutylene, methyl tertiary butyl ether, and methanol and also to provide a first higher boiling distillation fraction comprising methanol, tertiary butyl alcohol and water, by charging the first higher boiling distillation fraction to a recycle distillation column and fractionating it therein to provide a lower boiling recycle fraction comprising tertiary butyl alcohol and a higher boiling fraction comprising water and acidic by-products, by recycling the higher boiling water fraction to the MTBE distillation column at a charge point above the charge point for the etherification reaction product, and by adding aqueous sodium hydroxide to the recycled higher boiling fraction water in an amount sufficient to neutralize the acidic by-products charged to the MTBE distillation column.

The etherification reaction product obtained by reacting tertiary butyl alcohol with methanol will comprise methyl tertiary butyl ether, methanol, tertiary butyl alcohol, water, isobutylene, and acidic by-products including organic acids and esters such as methyl formate isobutyl formate, t-butyl acetate, etc. It is difficult to remove methyl formate from methyl tertiary butyl ether.

In accordance with a preferred embodiment of the present invention, the alkalinity of the recycled higher boiling fraction water is monitored and the amount of sodium hydroxide added to the recycled higher boiling fraction water is modified to compensate for a deviation in the alkalinity from a desired value.

DESCRIPTION OF PREFERRED EMBODIMENTS

I

In accordance with a preferred embodiment of the present invention, a method for the continuous preparation of methyl tertiary butyl ether from tertiary butyl alcohol, and methanol is provided which comprises:

a) continuously reacting methanol with tertiary butyl alcohol in a primary reactor to form an etherification reaction product comprising methanol, tertiary butyl alcohol, water, isobutylene, acidic by-products and methyl tertiary butyl ether;

b) continuously charging the etherification reaction product to a first methyl tertiary butyl ether distillation zone and separating it therein into a first lower boiling distillation fraction comprising methyl tertiary butyl ether, isobutylene, methanol and water and a first higher boiling distillation fraction comprising tertiary butyl alcohol, methanol acidic by-products and water;

c) charging the first higher boiling distillation fraction to a recycle distillation column and fractionating it therein to provide a lower boiling recycle fraction comprising tertiary butyl alcohol and a higher boiling fraction comprising acidic by-products and water;

d) recycling higher boiling water fraction to the first MTBE distillation column at a charge point above the charge point for the etherification reaction product; and e) adding aqueous sodium hydroxide to the recycled higher boiling water fraction in an amount sufficient to neutralize the acidic by-products charged to the MTBE distillation column.

In a more specific embodiment of the present invention:

a) methanol is continuously reacted with tertiary butyl alcohol in a primary reactor under reaction conditions including a pressure of about 30 to about 500 psia, and more preferably from about 200 to about 300 psia, a temperature of about 30° to about 200° C., and more preferably from about 80° to about 140° C., and still more preferably from about 90° to about 130° C., to form an etherification reaction product comprising methanol, tertiary butyl alcohol, water, isobutylene, acidic by-products including methyl formate, and methyl tertiary butyl ether;

b) the etherification reaction product is charged to a first MTBE distillation zone and fractionated therein under distillation conditions including a liquid reflux temperature of about 30° to about 100° C., and more preferably about 40° to about 80° C., a reboiler temperature of about 80° to about 115° C., and more preferably from about 95° to about 105° C., and a pressure of about 15 to about 60 psia to provide a first lower boiling distillation fraction comprising isobutylene, methyl tertiary butyl ether, methanol and acidic by-products and a first higher boiling distillation fraction comprising methanol, tertiary butyl alcohol and water, the distillation condition being selected such that substantially all of the MTBE in the etherification reaction product is taken with the first lower boiling distillation fraction;

c) the first higher boiling distillation fraction is charged to a recycle distillation column and fractionated therein under distillation conditions including a liquid reflux temperature of about 35° to about 170° C., and more preferably about 140° to about 150° C. and a reboiler temperature of about 100° to about 190° C., more preferably about 170° to about 180° C., and at a pressure of about 15 to about 190 psia, and more preferably about 110 to about 160 psia, to provide a lower boiling tertiary butyl alcohol recycle fraction and a higher boiling water fraction;

d) an alkaline solution of a sodium hydroxide is prepared by mixing aqueous sodium hydroxide with a portion of the higher boiling water fraction;

e) the alkaline recycle water fraction is recycled to the first MTBE distillation column at a charge point above the charge point for the etherification reaction product, in an amount sufficient to neutralize the acidic by-products charged to the MTBE distillation column; and f) the lower boiling recycle tertiary butyl alcohol fraction is recycled to the primary MTBE reactor.

In accordance with this embodiment, a measurement is made of the alkalinity of the alkaline recycle water fraction is made by measuring a property of the alkaline recycle water fraction (e.g., specific gravity) that is indicative of the alkalinity of the fraction and the amount of sodium hydroxide added to the recycle water fraction is adjusted in response to the measurement.

DETAILED DESCRIPTION OF THE PRESENT INVENTION

The Etherification Reaction Catalyst

In accordance with the MTBE manufacture and purification method of the present invention, an etherification reaction zone containing a bed of etherification catalyst is utilized. A wide variety of etherification catalysts can be used for this purpose, such as supported phosphorus acid-type catalysts. A preferred catalyst is a sulfonic acid resin etherification catalyst such as a sulfonated polystyrene resin cross-linked with divinyl benzene.

Any suitable solid resin etherification catalyst may be used for this purpose, such as a strongly acidic ion exchange resin consisting essentially of sulfonated polystyrene, such as a divinyl benzene crosslink polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

Also, Kieselguhr impregnated with phosphoric acid as disclosed in Frolich U.S. Pat. No. 2,282,469, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc., may be used.

Zeolites as disclosed in Japanese Patent 0007432 or aluminosilicate zeolites as disclosed in Chang et al. U.S. Pat. No. 4,058,576 may also be used.

The reaction conditions to be utilized when reacting methanol with tertiary butyl alcohol in the presence of a sulfonic acid resin etherification catalyst of the type disclosed in the prior art include a reaction temperature of about 90° to about 140° C., a pressure of about 30 to about 500 psia and a space velocity of about 0.5 to about 20 volumes of feed per volume of etherification catalyst per hour.

BRIEF DESCRIPTION OF THE DRAWING

The drawing is a schematic flow sheet with conventional parts omitted showing the general reaction and recovery sequence comprising of a preferred embodiment of the process of the present invention for the manufacture and purification of methyl tertiary butyl ether.

DESCRIPTION OF THE PREFERRED EMBODIMENT

Turning now to the Figure, there is shown a schematic flow sheet illustrating a preferred method for the practice of the process of the present invention. In the figure, conventional parts, such as valves, pumps, temperature control sensors, pressure sensors, heaters, coolers, flow control regulation apparatus, reflux condensers, reboilers, etc., have been omitted.

In accordance with the present invention, there is provided an etherification reaction zone 10 containing a bed of solid etherification catalyst. Any suitable etherification catalyst may be used such as, for example, a solid resin etherification catalyst of the type described above, such as a strongly acidic ion exchange resin consisting essentially of sulfonated polystyrene cross-linked with divinyl benzene (e.g., Dowex 50, Nalcite HCR, Amberlyst 15, etc.). As another example, the catalyst may be a fluorophosphoric acid-on-titania catalyst of the type disclosed in Knifton et al. U.S. Pat. No. 4,822,921 or a heteropoly acid such as 12-tungstophosphoric acid or 12-molybdophosphoric acid supported on an inert support such as titania.

Substantially peroxides-free tertiary butyl alcohol is continuously charged by a line 17 leading to a manifold 12. Methanol is continuously charged to the manifold 12 by a line 15. The flow of methanol and tertiary butyl alcohol to the manifold 12 through the lines 15 and 17 is regulated so that a molar excess of methanol is present in the line 15 leading to the etherification reaction zone 10, such as, for example, a molar ratio of about 1.1 to about 3 moles of methanol per mol of tertiary butyl alcohol.

Within the etherification reaction zone 10, the feed mixture is brought into contact with a bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., and still more preferably from about 90° to about 130° C. When the catalyst is a supported phosphorus acid-type catalyst, the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 10 and, more preferably from about 1 to about 4 volumes of feed mixture per volume of etherification catalyst per hour.

Within the etherification reaction zone 10, methanol will react with the tertiary butyl alcohol to form methyl tertiary butyl ether which will be contained in a reaction product discharged from the etherification reaction zone 10 by way of a line 20 leading to a first methyl tertiary butyl ether (MTBE) distillation column 30.

As a specific example, when the solid etherification catalyst is a sulfonic acid resin such as Amberlyst 15 and when the molar ratio of methanol to tertiary butyl alcohol in the feed mixture charged to the etherification reaction zone 10 by the line 14 is within the ratio of about 2.0 moles of methanol per mole of tertiary butyl alcohol, and the reaction is conducted at a temperature of about 110° C. at a feed rate of about 2.0 volumes of feed mixture per volume of catalyst per hour, the etherification reaction product may have the composition in part shown by the following table:

| ETHERIFICATION REACTION PRODUCT | |
| --- | --- |
| Component | wt. % (Approx.) |
| Water | 14.0 |
| Methanol | 27.6 |
| Isobutylene | 3.0 |
| TBA[1] | 14.1 |
| MTBE[2] | 34.5 |
| Other[3] | 6.8 |

[1]Tertiary butyl alcohol
[2]Methyl tertiary butyl ether
[3]Includes the acetone, propanol, ditertiary butyl peroxide, methyl formate, tertiary butyl formate, etc.

The etherification reaction product charged to the first MTBE distillation column 30 by way of the charge line 20 is fractionated therein under distillation conditions including a liquid reflux temperature of about 30° to about 100° C., and more preferably about 40° to about 80° C. a reboiler temperature of about 80° to about 115° C., and more preferably from about 95° to about 105° C., and a pressure of about 15 to about 60 psia, the distillation condition being selected such that substantially all of the MTBE in the etherification reaction product 20 is taken overhead from the first distillation column 30 by a line 32. As a consequence, the first lower boiling distillation fraction 32 taken overhead from the distillation zone 30 will comprise substantially all of the isobutylene, substantially all of the methyl tertiary butyl ether and some of the methanol charged to the first distillation zone 30. The acidic by-products that would normally be present in the lower boiling distillation fraction 32 are neutralized in the first distillation zone 30 in a manner to be described and the neutralized acids, including sodium formate, exit the distillation column 30 with the higher boiling fraction 34.

The methyl tertiary butyl ether in the line 32 is separated from the isobutylene and methanol by any suitable method (not shown) such as the method shown and described in Kruse et al. U.S. Pat. No. 5,243,091.

The first heavier distillation fraction 34 discharged from the first MTBE distillation zone 30 will comprise methanol, tertiary butyl alcohol neutralized acidic by-products and water.

The first heavier distillation fraction 34 is charged to a recycle distillation column 100 and fractionated therein under distillation conditions including a liquid reflux temperature of about 35° to about 170° C., and more preferably about 140° to about 150° C., and a reboiler temperature of about 100° to about 190° C., more preferably about 170° to about 180° C., and at a pressure of about 15 to about 190 psia, and more preferably about 110 to about 160 psia, to provide a lower boiling tertiary butyl alcohol recycle fraction 102 and a higher boiling water fraction 104.

The lower boiling tertiary butyl alcohol recycle fraction 102, comprising tertiary butyl alcohol and methanol is suitably recycled to the manifold 12 and thence by feed line 14 to the etherification reaction zone 10.

The higher boiling water fraction 104 is charged to a manifold 106 from which a part of the fraction 104 is recycled to the first MTBE distillation column 30 at a charge point above the charge point for the etherification reaction product 20. The remainder of the fraction 104 is discharged from the system through discard line 108 to prevent an undesired build-up of by-products in the system.

An aqueous solution of sodium hydroxide is prepared having a desired alkalinity (i.e., sodium hydroxide content), such as an aqueous solution containing about 15 to about 20 wt. % of sodium hydroxide. Such a solution will have a predeterminable specific gravity that can be changed by changing the amount of sodium hydroxide that is added to the aqueous solution of sodium hydroxide. The thus-prepared specific gravity-adjusted aqueous solution of sodium hydroxide of predetermined alkalinity is added to the recycle line 110 through a branch line 120 containing a control valve 122.

The aqueous solution of sodium hydroxide of predetermined alkalinity is added to the recycle line 110 through the branch line 120 in an amount sufficient to provide an alkaline recycle fraction 110 containing an amount of sodium hydroxide sufficient to neutralize the acidic by-products present in the MTBE distillation column 30, and to thereby form neutralized acidic by-products, including sodium formate, that descend the MTBE distillation column 30 for withdrawal with higher boiling water fraction 104. As indicated, a portion of the higher boiling water fraction 104 is discarded by the line 108 in order to prevent a build-up of neutralized acidic by-products in the system.

In accordance with this embodiment, a sample of the alkaline recycle fraction 110 is withdrawn by a sample line 130 and charged to a suitable device, such as a specific gravity meter 140, for measuring a physical property of the alkaline recycle fraction 110, such as specific gravity, which correlates with the alkalinity of the alkaline recycle fraction 110. A signal responsive to the measurement (e.g., a signal responsive to a determination of specific gravity in the specific gravity meter 140) is transmitted by a line 144 to the control 124 for the control valve 122 so that the setting of the control valve 122 can be changed in response to a measurement of the specific gravity of a sample supplied to the specific gravity meter 140.

What is claimed is:

1. An improved method for the manufacture of methyl tertiary butyl ether from tertiary butyl alcohol and methanol and for the removal of acidic by-products from the etherification reaction product which comprises:
   a) charging the etherification reaction product to a first MTBE distillation column and also charging a recycle higher boiling water fraction containing sodium hydroxide to said first MTBE distillation column and fractionating said etherification reaction product and said higher boiling recycle fraction therein to provide a first lower boiling distillation fraction substantially free from acidic by-products comprising isobutylene, methyl tertiary butyl ether, and methanol and a first higher boiling distillation fraction comprising methanol, tertiary butyl alcohol, neutralized acidic by-products and water,
   b) charging the first higher boiling distillation fraction to a recycle distillation column and fractionating it therein to provide a lower boiling recycle fraction comprising tertiary butyl alcohol and a higher boiling fraction comprising water and neutralized acidic by-products,
   c) recycling the higher boiling water fraction to the MTBE distillation column at a charge point above the charge point for the etherification reaction product, and
   d) adding aqueous sodium hydroxide to the recycled higher boiling water fraction in an amount sufficient to neutralize the acidic by-products charged to the MTBE distillation column.

2. A method as in claim 1 wherein the alkalinity of the recycled higher boiling water fraction is monitored and the amount of sodium hydroxide added to the recycled higher boiling water fraction is modified to compensate for a deviation in the alkalinity from a desired value.

3. A method for the continuous preparation of methyl tertiary butyl ether from tertiary butyl alcohol and methanol which comprises:
   a) continuously reacting methanol with tertiary butyl alcohol in a primary reactor under reaction conditions including a pressure of about 30 to about 500 psia, and a temperature of about 30° to about 200° C. to form an etherification reaction product comprising methanol, tertiary butyl alcohol, water, isobutylene, acidic by-products including methyl formate, and methyl tertiary butyl ether,
   b) continuously charging the etherification reaction product to a first MTBE distillation column and also charging an alkaline recycle water fraction to said first MTBE distillation column and fractionating said etherification reaction product and said alkaline recycle water fraction therein under distillation conditions including a liquid reflux temperature of about 30° to about 100° C., a reboiler temperature of about 80° to about 115° C. and a pressure of about 15 to about 60 psia to provide a first lower boiling distillation fraction substantially free from acidic by-products comprising isobutylene, methyl tertiary butyl ether, and methanol and a first higher boiling distillation fraction comprising methanol, tertiary butyl alcohol neutralized acidic by-products and water, the distillation conditions being selected such that substantially all of the MTBE in the etherification reaction product is taken with the first lower boiling distillation fraction,
   c) continuously charging said first higher boiling distillation fraction to a recycle distillation column and fractionating it therein under distillation conditions including a liquid reflux temperature of about 35° to about 170° C., and a reboiler temperature of about 100° to about 190° C. and a pressure of about 110 to about 160 psia, to provide a lower boiling tertiary butyl alcohol recycle fraction and a higher boiling water fraction containing neutralized acidic by-products,
   d) preparing an alkaline solution of sodium hydroxide by mixing aqueous sodium hydroxide with a portion of the higher boiling water fraction,
   e) recycling the alkaline recycle water fraction to the first MTBE distillation column at a charge point above the charge point for the etherification reaction product in an amount sufficient to neutralize the acidic by-products charged to the MTBE distillation column, and
   f) recycling the lower boiling recycle tertiary butyl fraction to the primary MTBE reactor.

4. A method as in claim 3 wherein the reaction conditions in the primary reactor include a pressure of about 200 to about 300 psia, and a temperature of about 80° to about 140° C.

5. A method as in claim 3 wherein the distillation conditions in the first MTBE distillation column include a liquid reflux temperature of about 40° to about 80° C. and a reboiler temperature of about 95° to about 105° C.

6. A method as in claim 3 wherein the distillation conditions in the recycle distillation column include a liquid reflux temperature of about 140° to about 150° C., and a reboiler temperature of about 170° to about 180° C.

7. A method as in claim 3 wherein the alkalinity of the recycled higher boiling water fraction is monitored and the amount of sodium hydroxide added to the recycled higher boiling water fraction is modified to compensate for a deviation in the alkalinity from a desired value.

8. A method as in claim 7 wherein a measurement of the alkalinity of the alkaline recycle water fraction is made by measuring the specific gravity of the alkaline recycle water fraction and by regulating the amount of sodium hydroxide added to the recycle water fraction in response to the measurement.

9. A method for the continuous preparation of methyl tertiary butyl ether from tertiary butyl alcohol and methanol which comprises:
   a) continuously reacting methanol with tertiary butyl alcohol in a primary MTBE reactor to form an etherification reaction product comprising methyl tertiary butyl ether, methanol, tertiary butyl alcohol, water, isobutylene and acidic by-products,
   b) continuously charging the etherification reaction product to a first MTBE distillation zone together with an alkaline recycle water fraction, whereby said acidic by-products will be neutralized and fractionating said etherification reaction product therein to provide a first lower boiling distillation fraction substantially free from acidic by-products comprising methyl tertiary butyl ether, isobutylene and methanol and a first higher boiling fraction comprising methanol, tertiary butyl alcohol, water and said neutralized acidic by-products, c) continuously charging said first higher boiling fraction to a recycle distillation column and fractionating it therein to provide a lower boiling tertiary butyl alcohol recycle fraction and a higher boiling water fraction, d) discarding a first portion of said higher boiling water fraction, e) preparing an alkaline recycle water fraction by mixing aqueous sodium hydroxide with a second portion of said higher boiling water fraction, f) recycling said alkaline recycle water fraction to the first MTBE distillation column at a charge point above the charge point for the etherification reaction product in an amount sufficient to neutralize the acidic by-products charged to the MTBE distillation column, and g) recycling the lower boiling recycle tertiary butyl alcohol recycle fraction to the primary MTBE reactor.

10. A method as in claim 9 wherein the alkalinity of the second portion of the higher boiling water fraction is monitored and the amount of sodium hydroxide added to the second portion of the higher boiling water fraction is modified to compensate for a deviation in the alkalinity from a desired value.

11. A method as in claim 10 wherein a measurement of the alkalinity of the alkaline recycle water fraction is made by measuring the specific gravity of the alkaline recycle water fraction and by regulating the amount of sodium hydroxide added to the recycle water fraction in response to the measurement.

* * * * *